United States Patent
Lincoln et al.

(10) Patent No.: US 7,177,685 B2
(45) Date of Patent: Feb. 13, 2007

(54) CLASSIFYING TACHYARRHYTHMIA USING TIME INTERVAL BETWEEN VENTRICULAR DEPOLARIZATION AND MITRAL VALVE CLOSURE

(75) Inventors: William C. Lincoln, Coon Rapids, MN (US); Gerrard M. Carlson, Champlin, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 562 days.

(21) Appl. No.: 10/618,261

(22) Filed: Jul. 11, 2003

(65) Prior Publication Data

US 2005/0010257 A1 Jan. 13, 2005

(51) Int. Cl.
*A61N 1/365* (2006.01)
*A61N 1/39* (2006.01)
*A61B 5/04* (2006.01)

(52) U.S. Cl. ................ 607/18; 607/6; 607/14; 600/514; 600/515; 600/516; 600/518

(58) Field of Classification Search ............... 600/508, 600/514–516, 518, 521; 607/6, 18, 25
See application file for complete search history.

(56) References Cited

U.S. PATENT DOCUMENTS

| | | | |
|---|---|---|---|
| 5,674,256 A | 10/1997 | Carlson | |
| 6,643,548 B1 * | 11/2003 | Mai et al. | 607/17 |
| 6,665,564 B2 | 12/2003 | Lincoln et al. | |
| 2002/0151938 A1 * | 10/2002 | Corbucci | 607/25 |

OTHER PUBLICATIONS

Brooks, Nicholas, et al., "Factors responsible for normal splitting of first heart sound", *British Heart Journal, vol. 42*, (1979), 695-702.

Manyari, Dante, et al., "A Simple Echocardiographic Method to Detect Atrioventricular Dissociation", *Chest, vol. 81, No. 1*, (Jan. 1982), 67-73.

Ruckel, Andreas, et al., "Atrioventricular Dissociation Detected by Suprastemal M-Mode Echocardiography: A Clue to the Diagnosis of Ventricular Tachycardia", *Am J. Cardiol, vol. 54.*, (1984), 561-563.

* cited by examiner

*Primary Examiner*—Robert Pezzuto
*Assistant Examiner*—Yun Haeng Lee
(74) *Attorney, Agent, or Firm*—Schwegman Lundberg Woessner & Kluth

(57) ABSTRACT

A cardiac rhythm management system measures a time interval between a first fiducial marker indicative of a ventricular depolarization (e.g., a Q-wave, an R-wave, etc.) and a second fiducial marker indicative of a subsequent mitral valve closure (MVC) occurring during the same cardiac cycle. Such time intervals are used for detecting atrioventricular (AV) dissociation. The AV dissociation may, in turn, be used for discriminating between a supraventricular tachyarrhythmia (SVT) and a ventricular tachyarrhythmia (VT) or for any other diagnostic or therapeutic purpose. The AV dissociation and/or SVT/VT discrimination information may be communicated from an implantable cardiac rhythm management device to an external interface and/or used to determine the nature of therapy delivered to the subject. In a further example, amplitudes indicative of the MVCs are also used for determining whether AV dissociation exists.

50 Claims, 4 Drawing Sheets

CLASSIFYING TACHYARRHYTHMIA USING TIME INTERVAL BETWEEN VENTRICULAR DEPOLARIZATION AND MITRAL VALVE CLOSURE

TECHNICAL FIELD

The present system relates generally to cardiac rhythm management systems and particularly, but not by way of limitation, to classifying a tachyarrhythmia using a time interval between a ventricular depolarization and a mitral valve closure.

BACKGROUND

A cardiac rhythm management system may include an implantable cardiac rhythm management device. Such devices may provide therapy, such as to treat bradyarrhythmias and/or tachyarrhythmias. In addition to adjusting heart rate, such a device may also improve cardiac output by providing cardiac resynchronization therapy (CRT). Such CRT assists in spatially coordinating heart contractions. Different arrhythmias and/or pathological conditions may require different therapies. For example, a supraventricular tachyarrhythmia (SVT) may be treated differently from a ventricular tachyarrhythmia (VT). Therefore, it may be desirable for the system to distinguish SVT from VT.

One factor useful for identifying VT (such as for discriminating between SVT and VT, or otherwise) is detecting atrioventricular (AV) dissociation, in which the ventricular heart rhythm doesn't track the atrial heart rhythm. The existence of AV dissociation during a tachyarrhythmia is often an indicator of the existence of VT rather than SVT, particularly where the VT or SVT occurs during a regular heart rhythm.

SUMMARY

The present inventors have recognized that certain techniques of detecting AV dissociation require detecting atrial depolarizations (often referred to as a "P-wave") on an electrocardiographic (ECG) or similar heart signal. However, the present inventors have recognized that some patients manifest wide ventricular depolarizations (often referred to as QRS complexes) on the ECG signal. Such wide QRS complexes may mask the P-wave. This may confound detection of AV dissociation techniques that use P-wave detection, which may, in turn, confound discrimination between VT and SVT. Accordingly, the present inventors have recognized a need for obtaining additional information useful for detecting AV dissociation and/or discriminating between VT and SVT using the AV dissociation, where appropriate. The present inventors have further recognized that such additional information could be useful not only where P-wave information is difficult to obtain, but also where P-wave information is more readily obtainable.

Accordingly, the present document discloses cardiac rhythm management systems, devices, and methods that measure a time interval between a first fiducial marker correlative to a ventricular depolarization (e.g., a QRS complex, a Q-wave, an R-wave, etc.) and a second fiducial marker correlative to a subsequent mitral valve closure (MVC) occurring during the same cardiac cycle. Such time intervals are used for detecting AV dissociation. The AV dissociation may, in turn, be used—particularly during a regular heart rhythm—for discriminating between a supraventricular tachyarrhythmia (SVT) and a ventricular tachyarrhythmia (VT) or for any other diagnostic and/or therapeutic purpose. AV dissociation occurring during a VT is referred to as AV dissociated VT, or simply dissociated VT. The AV dissociation and/or SVT/VT discrimination information may be communicated from an implantable cardiac rhythm management device to an external interface and/or used to determine the nature of therapy delivered to the subject. Other aspects of the present cardiac rhythm management systems, devices, and methods will become apparent upon reading the following detailed description and viewing the drawings that form a portion thereof.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

Figure 1:
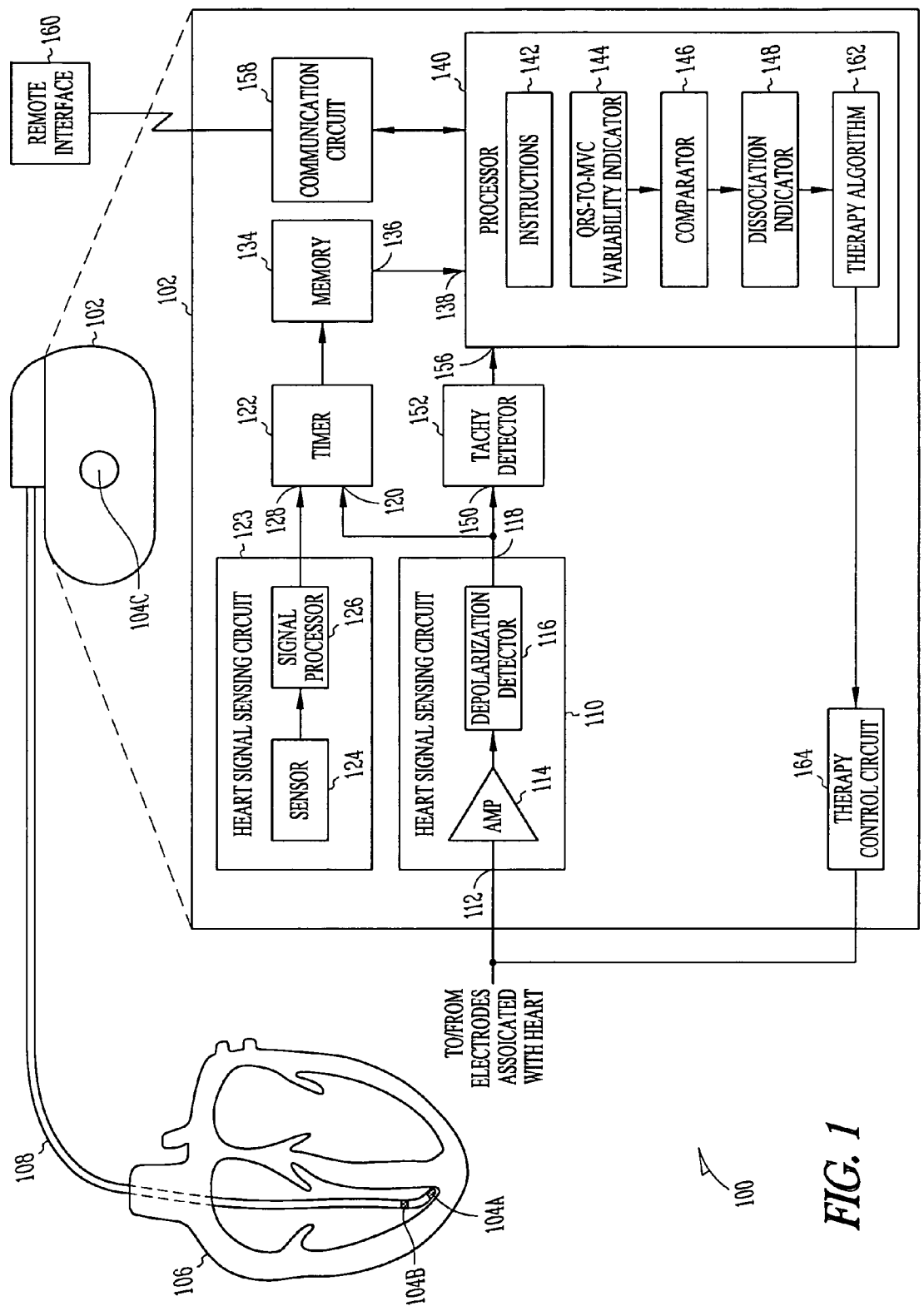
FIG. 1 is a schematic/block diagram illustrating generally, among other things, one example of portions of a cardiac rhythm management system and an environment in which it is used.

In the following detailed description, reference is made to the accompanying drawings which form a part hereof, and in which is shown by way of illustration specific embodiments in which the invention may be practiced. These embodiments, which are also referred to herein as "examples," are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not to be taken in a limiting sense, and the scope of the present invention is defined by the appended claims and their equivalents. In the drawings, like numerals describe substantially similar components throughout the several views. Like numerals having different letter suffixes represent different instances of substantially similar components.

The present systems, devices, and methods will be described in applications involving implantable medical devices including, but not limited to, implantable cardiac rhythm management devices such as pacemakers, cardioverter/defibrillators, pacer/defibrillators, biventricular or other multi-site coordination and/or cardiac resynchronization devices, and drug delivery systems. However, it is understood that the present methods and apparatus may be employed in unimplanted devices, including, but not limited to, external pacemakers, cardioverter/defibrillators, pacer/defibrillators, biventricular or other multi-site coordination and/or cardiac resynchronization devices, monitors, programmers and recorders, whether such devices are used for providing a diagnostic, a therapy, or both a diagnostic and a therapy.

FIG. 1 is a schematic diagram illustrating generally one example of portions of the present cardiac rhythm management system 100 and an environment in which it is used. In this embodiment, system 100 includes, among other things, an implantable or other cardiac rhythm management device 102. The device 102 is coupled to at least one electrode 104 associated with the heart 106, such as via an intravascular lead 108, or via at least one electrode 104C located on a housing of the implantable device 102.

In one example, the electrode is "associated" with the particular heart chamber by inserting it into that heart chamber, or by inserting it into a portion of the heart's vasculature that is close to that heart chamber, or by epicardially placing the electrode outside that heart chamber, or by any other technique of configuring and situating an electrode for sensing signals and/or providing therapy with respect to that heart chamber. Device 102 may also include other electrodes, such as a housing electrode and/or a header electrode, or even one or more external electrodes, such as may be affixed to the subject's skin.

In the example of FIG. 1, device 102 includes a heart signal sensing circuit 110 having at least one input 112 coupled to electrode(s) 104 associated with the heart 106. The heart signal sensing circuit 110 typically includes an amplifier 114 to receive an intrinsic ventricular heart signal. An output of the amplifier 114 is coupled to an input of a depolarization detector circuit 116, such as a level detector and/or peak detector circuit, to detect a ventricular depolarization. The ventricular depolarization is typically referred to as a QRS complex. The QRS complex is comprised of a sequence of deviations from baseline referred to as a Q-wave, an R-wave, and an S-wave. The QRS complex and its constituent deviations are examples of indications of a ventricular depolarization. Upon detecting such a QRS complex, the depolarization detector circuit 116 captures a system clock time value corresponding to the occurrence of the detected QRS complex. An output 118 of the heart signal sensing circuit 110 provides information about the times corresponding to the detected ventricular depolarization indications. The output 118 of the heart signal sensing circuit 110 is coupled to a first input 120 of a timer circuit 122.

In the example of FIG. 1, device 102 also includes a mitral valve closure sensing circuit 123. The mitral valve closure sensing circuit 123 typically includes a sensor 124, such as an accelerometer (for sensing acceleration or vibrations) and/or a microphone (for sensing acoustic energy). The mitral valve closure sensing circuit 123 also typically includes a signal processing circuit 126, which is coupled to the sensor 124. The signal processing circuit 126 outputs information about the times indicative of mitral valve closures and/or heart sounds (such as the S1 heart sound) that include information indicative of a mitral valve closure. The signal processing circuit 126 outputs these times indicative of mitral valve closures to a second input 128 of the timer circuit 122.

In the example of FIG. 1, the timer circuit 122 measures time intervals. Each time interval is measured between the time indicative of the ventricular depolarization and the time indicative of a subsequent MVC occurring during the same cardiac cycle. The timer circuit 122 includes an output 130 that is coupled to an input 132 of a memory circuit 134. The memory circuit 134 stores the time intervals. The memory circuit 134 includes an output 136 that provides the stored time intervals to at least one input 138 of a processor circuit 140. The processor circuit 140 includes executable instructions 142 for computing a QRS-to-MVC variability indicator 144 (e.g., a range, a variance, a standard deviation, etc.) of the time intervals.

In one example, the variability indicator 144 is provided to a comparator 146 and compared against a predetermined threshold value. If the variability indicator 144 exceeds the threshold value, then a binary or other dissociation indicator 148 is set to "true," or to otherwise indicate that a dissociation condition exists. In a further example, the output 118 of the heart signal sensing circuit 110 is also coupled to an input 150 of a tachyarrhythmia detector circuit 152. In one example, the tachyarrhythmia detector circuit 152 deems a tachyarrhythmia to exist when a rate between ventricular depolarizations exceeds a predetermined threshold value. An output 154 of the tachyarrhythmia detector circuit 152 is coupled to an input 156 of the processor circuit 140. In this example, the processor circuit 140 deems a ventricular tachyarrhythmia (VT) dissociation condition to exist when both a tachyarrhythmia is present and the dissociation indicator 148 is true.

In a further example, the device 102 may include a communication circuit 158 that wirelessly or otherwise communicates information indicative of whether a dissociation condition or a VT dissociation exists to an external programmer or other remote interface 160, such as for display to a physician or other caregiver. In another example, the dissociation indicator 148 is used by a therapy algorithm 162 that controls timing of delivery of anti-tachyarrhythmia or other cardiac rhythm management therapy provided by therapy control circuit 164 to the heart 106 based at least in part on whether the VT dissociation exists. In yet another example, the described indicator of whether VT dissociation exists is used in combination with one or more other similar indicators obtained using different techniques, such as to increase the accuracy of the VT dissociation and/or SVT/VT discrimination determination.

Thus, the example device 102 illustrated in FIG. 1 is capable of determining whether a dissociated VT exists using only detected ventricular depolarizations and detected MVCs. This avoids any need to detect a P-wave associated with an atrial depolarization. This is particularly useful where no atrial electrode is available, or where the P-wave is obscured by a wide QRS complex, thereby making the P-wave difficult to detect. This also avoids any need to use echocardiographic techniques that are typically not well suited to an implantable device 102.

Figure 2:
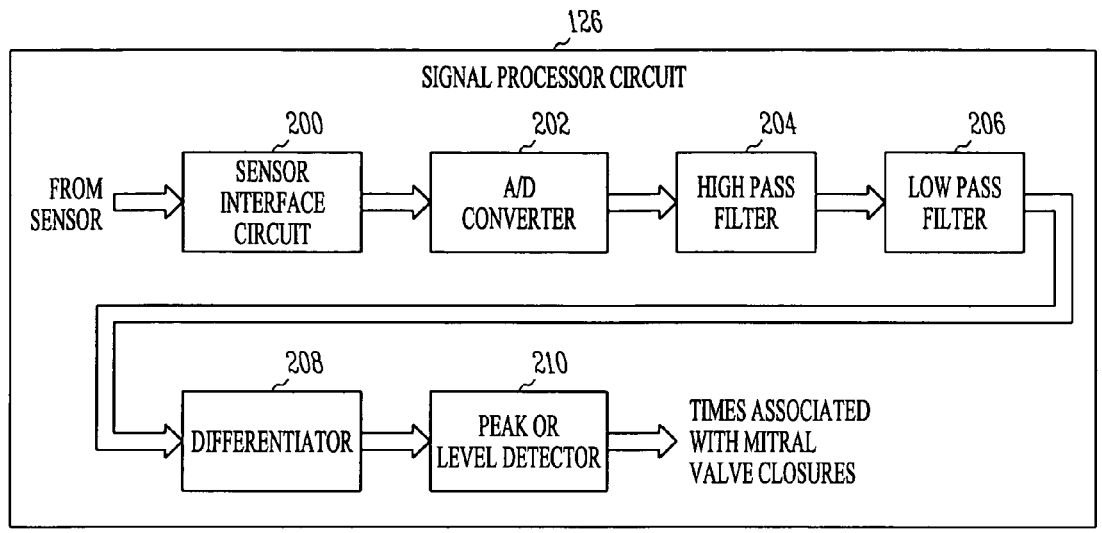
FIG. 2 is a schematic/block diagram illustrating generally one example of portions of a signal processing circuit for detecting mitral valve closures (MVCs).

FIG. 2 is a schematic diagram illustrating generally, by way of example, but not by way of limitation, one example of portions of the signal processor circuit 126 used for detecting MVCs. In the example of FIG. 2, the signal processor circuit 126 includes a sensor interface circuit 200, an analog-to-digital (A/D) converter circuit 202, a highpass filter circuit 204, a lowpass filter circuit 206, a differentiator circuit 208, and a peak or level detector circuit 210. An input of the sensor interface circuit 200 is coupled to the sensor 124, such as to receive an acceleration or sound signal that includes information about MVCs. The sensor interface circuit 200 typically includes an amplifier circuit and any analog filtering circuits, such as an anti-aliasing filter circuit. An output of the sensor interface circuit 200 is coupled to an input of the A/D converter 202 to provide it with a sensor signal that is suitable for digitizing into an 8-bit, 10-bit, or other suitable digital sensor signal. At least one output of the A/D converter 202 is coupled to at least one input of the highpass filter circuit 204 to provide it with a digital sensor signal suitable for further digital signal processing. The highpass filter circuit 204 removes or attenuates a baseline component of the digital sensor signal, such as by using a highpass filter having an effective cutoff frequency of about 1 Hz. At least one output of the highpass filter circuit 204 is coupled to at least one input of the lowpass filter 206. The lowpass filter 206 removes a high frequency component of its input signal, such as by using 5-sample moving average "boxcar" filter attenuating signal frequencies above approximately 100 Hz. At least one output of the lowpass filter 206 is coupled to at least one input of the differentiator 208. At least one output of the differentiator circuit 208 is coupled to at least one input of the peak or level detector 210 to provide it with a signal having a first peak occurring between the ventricular heart contraction and a subsequent atrial heart contraction. This first peak is indicative of a MVC. The peak or level detector circuit 210 detects such peaks that are indicative of MVC using either peak or level detecting techniques, or both. Upon detecting such an MVC, the peak or level detector circuit 210 captures a system clock time value corresponding to the occurrence of the detected MVC. At least one output of the peak or level detector circuit 210 provides times associated with the MVCs to the timer circuit 122 for measuring the QRS-to-MVC time intervals, as discussed above. Other aspects of one suitable example of the signal processor circuit 126 is described in commonly assigned Lincoln et al. U.S. patent application Ser. No. 09/862,763, filed on May 21, 2001, entitled CARDIAC RHYTHM MANAGEMENT SYSTEM DETECTING AV-DELAY BASED ON INTERVAL BETWEEN ATRIAL DEPOLARIZATION AND MITRAL VALVE CLOSURE, which is incorporated herein by reference in its entirety, including its description of an MVC fiducial point generator and associated signal processing circuitry for obtaining MVC information.

Figure 3:
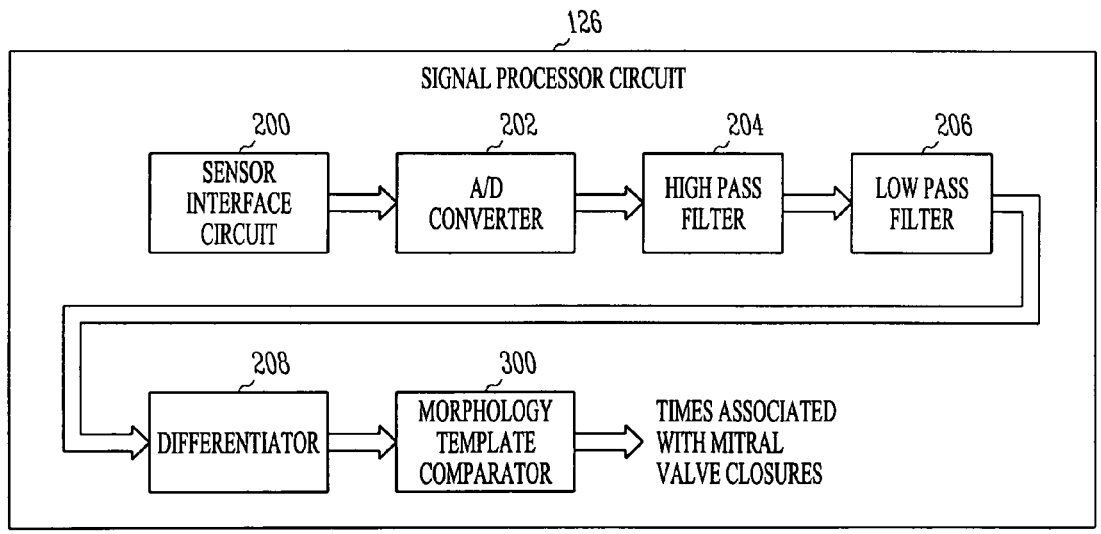
FIG. 3 is a schematic/block diagram illustrating generally another example of portions of a signal processing circuit for detecting MVCs, such as by using a matching filter comparing a morphology to a template.

FIG. 3 is a schematic diagram illustrating generally, by way of example, but not by way of limitation, an alternative example of the signal processor circuit 126. In this example, a morphology template comparator 300 or other signal matching type filter is substituted for the peak or level detector circuit 210. The morphology template comparator 300 includes a stored template of a portion of an input signal that is indicative of a MVC. The morphology template comparator 300 compares the shape of a portion of its input signal to the stored template indicative of a MVC, such as by using auto-regression or similar techniques. When a close enough match is obtained, a MVC is declared. One example of matching a portion of a signal to a template is described in commonly assigned Carlson U.S. Pat. No. 5,674,256 entitled CARDIAC PRE-EJECTION PERIOD DETECTION, which is incorporated herein by reference in its entirety, including its description of autoregression and template matching to detect a signal feature, such as the present indications of MVCs.

Figure 4:
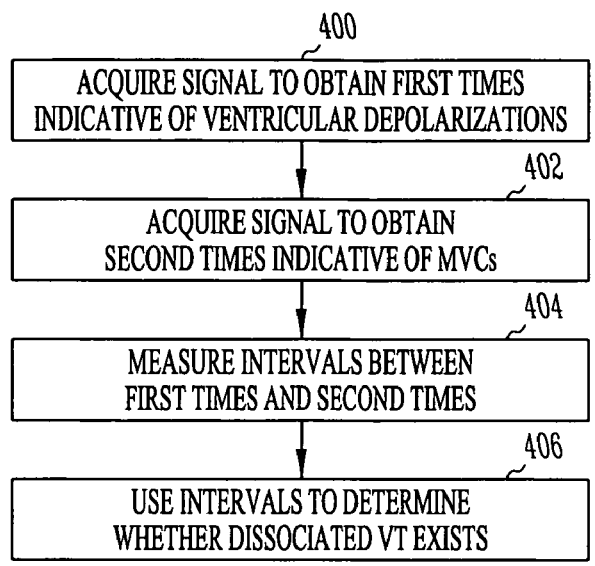
FIG. 4 is a flow chart illustrating generally one example technique for determining whether a dissociation condition exists.

FIG. 4 is a flow chart illustrating generally, by way of example, but not by way of limitation, one example of a method of determining whether a dissociated VT exists. At 400, a signal is acquired to obtain first times that are indicative of ventricular depolarizations. In one example, this includes acquiring an electrical intrinsic ventricular heart signal from at least one intravascular, housing, surface, or other electrode 104 associated with the heart 106. In another example, such as when the ventricular depolarization results from issuance of a pacing stimulus, the first time is instead measured from the time of issuance of the pacing stimulus or, alternatively, measured from the time at which an evoked response QRS complex is detected. At 402, another signal is acquired to obtain second times that are indicative of MVCs, such as by using one or more of the various techniques described above. In one example, this MVC information is obtained from an acceleration or vibration signal provided by an accelerometer located within the implantable device 102 or elsewhere. In another example, this MVC information is obtained from an acoustic signal provided by a microphone located within the implantable device 102, such as on an intravascular lead, or elsewhere. At 404, QRS-to-MVC time intervals are measured between the first times and the second times, such as by using the timer circuit 122. At 406, these time intervals are used to determine whether a dissociated VT exists, such as by comparing a variability (e.g., range, variance, standard deviation, etc.) of the time intervals to a predetermined threshold value and, if such variability exceeds the threshold value, then declaring a dissociation condition to exist. In one illustrative example, the QRS-to-MVC time intervals for the most recent 20 heart beats are collected, and a variability is calculated. In this illustrative example, if the variability exceeds a predetermined threshold value, then a dissociation condition is declared.

Figure 5:
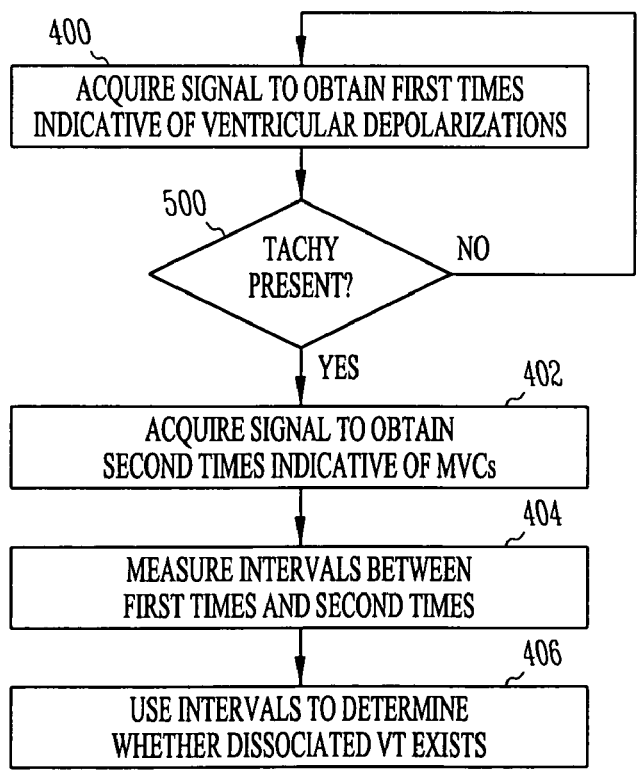
FIG. 5 is a flow chart illustrating generally another example technique for determining whether a dissociation condition, such as dissociated ventricular tachyarrhythmia (VT) exists.

FIG. 5 is a flow chart illustrating generally, by way of example, but not by way of limitation, a further technique for determining whether dissociated VT exists. In the example of FIG. 5, as first times indicative of ventricular depolarizations are being obtained on a beat-by-beat basis at 400, a determination of whether a tachyarrithmia is present is made at 500. In one example, the rate between successive ventricular depolarizations is compared to a tachyarrhythmia rate threshold (e.g., 100 beats per minute) and, if this ventricular rate exceeds the tachyarrhythmia rate threshold, then a tachyarrhythmia is declared present. In this example, only if a tachyarrhythmia is declared present at 500 are the subsequent acts 402, 404, and 406 carried out.

Figure 6:
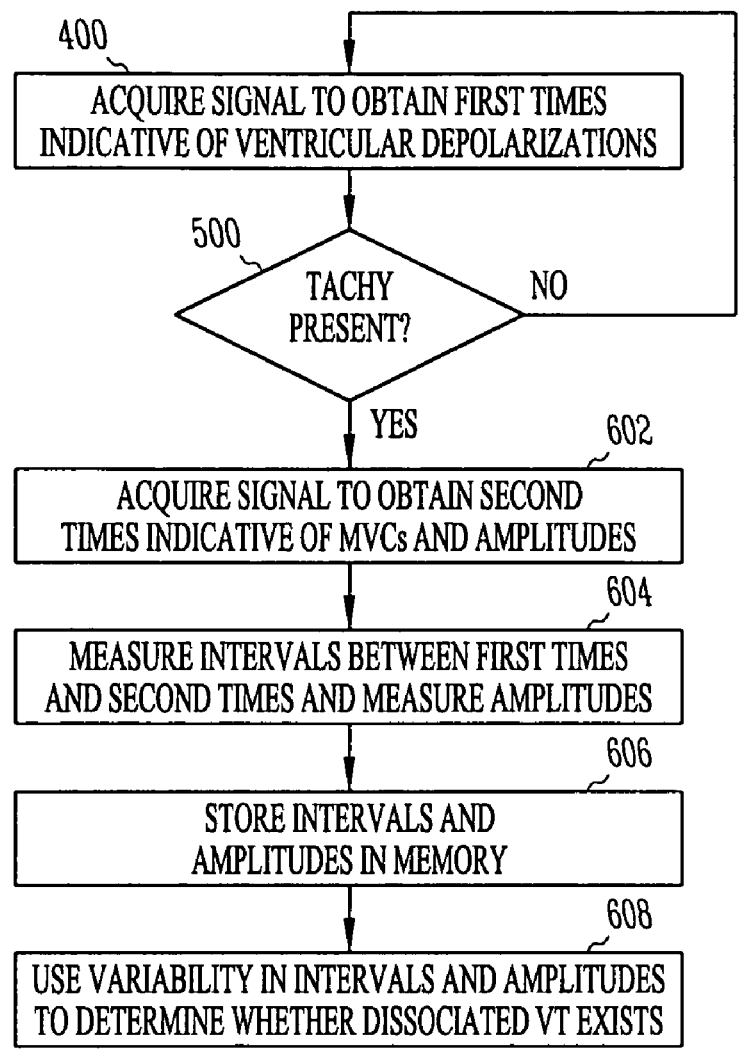
FIG. 6 is a flow chart illustrating generally, by way of example, but not by way of limitation, a further technique for determining whether dissociated VT exists.

FIG. 6 is a flow chart illustrating generally, by way of example, but not by way of limitation, a further technique for determining whether dissociated VT exists. This technique is similar to FIG. 5 is some respects, however, both second times indicative of MVCs and corresponding signal amplitudes are acquired at 602 (such as where peak or level detector 210 is implemented as a peak detector). At 604, QRS-to-MVC intervals between the first and second times are measured, and amplitudes of the processed digital sensor signal are also measured. At 606, the QRS-to-MVC intervals and amplitudes are stored in memory. At 608, variability in the intervals and/or the amplitudes is used to determine whether a dissociated VT exists. In one example, this includes comparing a percent range (or other statistical variability indicator) of the intervals to a corresponding first predetermined threshold, as discussed above. A percent range (or other statistical variability indicator) of the amplitudes is similarly compared to a corresponding second predetermined threshold. Only if both such variabilities exceed their thresholds is a ventricular dissociation condition deemed to exist.

It is to be understood that the above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein."

What is claimed is:

1. A system comprising a processor circuit with executable instructions to determine whether a dissociated ventricular tachyarrhythmia exists using time intervals, in which each time interval is between a first time indicative of a ventricular depolarization and a second time indicative of a mitral valve closure.

2. The system of claim 1, further comprising:
a heart signal sensing circuit, comprising a depolarization detector circuit to detect first times indicative of ventricular depolarizations occurring during cardiac cycles;
a mitral valve closure sensor circuit, to detect second times indicative of mitral valve closures;
a timer circuit, coupled to the heart signal sensing circuit and to the mitral valve closure sensor circuit, to measure time intervals between one of the first times and one of the second times within the same cardiac cycle; and
a memory circuit, coupled to the timer circuit, the memory circuit configured to store the time intervals.

3. The system of claim 2, in which the depolarization detector circuit comprises:
an amplifier circuit; and
at least one of a level detector circuit and a peak or level detector circuit, coupled to the amplifier circuit.

4. The system of claim 2, in which the mitral valve closure sensor circuit comprises an accelerometer.

5. The system of claim 2, in which the mitral valve closures sensor circuit comprises a microphone.

6. The system of claim 2, in which the mitral valve closure sensor circuit includes a highpass filter circuit.

7. The system of claim 2, in which the mitral valve closure sensor circuit comprises a differentiator circuit.

8. The system of claim 2, in which the mitral valve closure sensor circuit comprises a lowpass filter circuit.

9. The system of claim 2, in which the mitral valve closure sensor circuit comprises a peak or level detector circuit.

10. The system of claim 2, in which the mitral valve closure sensor circuit comprises a sensor, including at least one of an accelerometer and a microphone, to provide a sensor signal.

11. The system of claim 10, in which the mitral valve closure sensor circuit comprises:
means, coupled to the sensor, for removing a baseline component of the sensor signal;
a lowpass filter circuit, coupled to the means for removing the baseline component of the sensor signal, to filter the sensor signal; and
a peak or level detector circuit, coupled to the lowpass filter circuit.

12. The system of claim 10, in which the mitral valve closure sensor circuit comprises a morphology template comparator including a template to compare the sensor signal against to detect the second times indicative of mitral valve closures.

13. The system of claim 1, in which the processor circuit includes executable instructions to compute at least one of a variance, a range, and a standard deviation of the time intervals to determine whether a dissociated tachyarrhythmia exists.

14. The system of claim 1, further comprising a lead coupled to the heart signal sensing circuit.

15. The system of claim 1, further comprising a communication circuit to communicate an indication of whether a dissociated ventricular tachyarrhythmia exists to a remote location.

16. The system of claim 15, further comprising a remote interface to receive the indication of whether the dissociated ventricular tachyarrhythmia exists from the communication circuit.

17. The system of claim 1, in which the executable instructions to determine whether a dissociated ventricular tachyarrhythmia exists also use an indicator of variability of amplitudes of mitral valve closures.

18. A system comprising:
a heart signal sensing circuit, comprising a depolarization detector circuit to detect first times indicative of ventricular depolarizations occurring during cardiac cycles;
a mitral valve closure sensor circuit, to detect second times indicative of mitral valve closures;
a timer circuit, coupled to the heart signal sensing circuit and to the mitral valve closure sensor circuit, to measure time intervals between one of the first times and one of the second times within the same cardiac cycle;
a memory circuit, coupled to the timer circuit, the memory circuit configured to store the time intervals; and
a processor circuit, coupled to or including the memory circuit, the processor circuit including executable instructions to determine whether a dissociated tachyarrhythmia exists using the time intervals.

19. The system of claim 18, in which the depolarization detector circuit comprises:
an amplifier circuit; and
at least one of a level detector circuit and a threshold detector circuit, coupled to the amplifier circuit.

20. The system of claim 18, in which the mitral valve closure sensor circuit comprises an accelerometer.

21. The system of claim 18, in which the mitral valve closures sensor circuit comprises a microphone.

22. The system of claim 18, in which the processor circuit includes executable instructions to compute at least one of a variance, a range, and a standard deviation of the time intervals to determine whether a dissociated tachyarrhythmia exists.

23. The system of claim 18, in which the mitral valve closure sensor circuit includes a highpass filter circuit.

24. The system of claim 18, in which the mitral valve closure sensor circuit comprises a differentiator circuit.

25. The system of claim 18, in which the mitral valve closure sensor circuit comprises a lowpass filter circuit.

26. The system of claim 18, in which the mitral valve closure sensor circuit comprises a peak or level detector circuit.

27. The system of claim 18, in which the mitral valve closure sensor circuit comprises a sensor, including at least one of an accelerometer and a microphone, to provide a sensor signal.

28. The system of claim 27, in which the mitral valve closures sensor circuit compnses:
means, coupled to the sensor, for removing a baseline component of the sensor signal;

a lowpass filter circuit, coupled to the means for removing the baseline component of the sensor signal, to filter the sensor signal; and a peak or level detector circuit, coupled to the lowpass filter circuit.

29. The system of claim 27, in which the mitral valve closure sensor circuit comprises a template to compare the sensor signal against to detect the second times indicative of mitral valve closures.

30. The system of claim 18, further comprising a lead coupled to the heart signal sensing circuit.

31. The system of claim 18, further comprising a communication circuit to communicate an indication of whether a dissociated ventricular tachyarrhythmia exists to a remote location.

32. The system of claim 31, further comprising a remote interface to receive the indication of whether the dissociated ventricular tachyarrhythmia exists from the communication circuit.

33. The system of claim 18, in which the executable instructions to determine whether a dissociated ventricular tachyarrhythmia exists also use an indicator of variability of amplitudes of mitral valve closures.

34. A method comprising:
acquiring a first signal to obtain first times indicative of ventricular depolarizations;
acquiring a second signal to obtain second times indicative of mitral valve closures occurring during respective cardiac cycles of the ventricular depolarizations;
measuring time intervals, each of the time intervals measured between one of the first times and one of the second times within the same cardiac cycle; and
determining whether a dissociated ventricular tachyarrhythmia exists using the time intervals.

35. The method of claim 34, in which the acquiring the first signal includes acquiring an electrical heart signal.

36. The method of claim 34, in which the acquiring the second signal comprises acquiring an acceleration signal.

37. The method of claim 34, in which the acquiring the second signal comprises acquiring a sound signal.

38. The method of claim 34, in which the determining whether a dissociated ventricular tachyarrhythmia exists comprises computing a statistic using the time intervals.

39. The method of claim 38, in which the determining whether a dissociated ventricular tachyarrhythmia exists further comprises comparing the statistic to a predetermined threshold value.

40. The method of claim 38, in which the computing the statistic comprises computing a range of values of the time intervals.

41. The method of claim 38, in which the computing the statistic comprises computing a variance of the time intervals.

42. The method of claim 38, in which the computing the statistic comprises computing a standard deviation of the time intervals.

43. The method of claim 34, in which the acquiring the second signal comprises attenuating a baseline component of the second signal.

44. The method of claim 43, in which the attenuating the baseline component of the second signal includes highpass filtering the second signal.

45. The method of claim 43, in which the attenuating the baseline component of the second signal includes differentiating the second signal.

46. The method of claim 45, further comprising lowpass filtering the second signal.

47. The method of claim 46, in which the acquiring a second signal to obtain the second times includes detecting peaks of the second signal after the attenuating the baseline component and the lowpass filtering of the second signal.

48. The method of claim 34, in which the acquiring a second signal to obtain the second times includes comparing at least a portion of the second signal to a template.

49. The method of claim 34, further comprising communicating an indication of whether a ventricular tachyarrhythmia exists to a remote location.

50. The method of claim 34, further comprising:
measuring amplitudes of the second signal at the second times; and
in which the determining whether a dissociated ventricular tachyarrhythmia exists also includes using the amplitudes.

* * * * *

UNITED STATES PATENT AND TRADEMARK OFFICE
CERTIFICATE OF CORRECTION

| | | |
|---|---|---|
| PATENT NO. | : 7,177,685 B2 | Page 1 of 1 |
| APPLICATION NO. | : 10/618261 | |
| DATED | : February 13, 2007 | |
| INVENTOR(S) | : Lincoln et al. | |

It is certified that error appears in the above-identified patent and that said Letters Patent is hereby corrected as shown below:

Title Page;
On Sheet 1 of 4, in FIG. 1 (Beside Reference Numeral 112), line 3, delete "ASSOICATED" and insert -- ASSOCIATED --, therefor.

In column 8, line 65, in Claim 28, delete "compnses" and insert -- comprises --, therefor.

Signed and Sealed this

Fifteenth Day of May, 2007

JON W. DUDAS
*Director of the United States Patent and Trademark Office*